(12) United States Patent
Hassler et al.

(10) Patent No.: US 6,997,958 B2
(45) Date of Patent: Feb. 14, 2006

(54) CONICAL COUPLING AND PROSTHESIS COMPRISING SUCH A COUPLING

(75) Inventors: Michel Hassler, St. Ismier (FR); Cécile Real, Grenoble (FR); Jean-Pierre Pequignot, Nice (FR); Philippe De Mourgues, La Motte Servoles (FR); Yves Allieu, Montpellier (FR)

(73) Assignee: Bioprofile, Grenoble (FR)

(*) Notice: Subject to any disclaimer, the term of this patent is extended or adjusted under 35 U.S.C. 154(b) by 179 days.

(21) Appl. No.: 10/442,045

(22) Filed: May 21, 2003

(65) Prior Publication Data

US 2004/0030401 A1    Feb. 12, 2004

(30) Foreign Application Priority Data

May 22, 2002  (FR) .................................. 02 06196

(51) Int. Cl.
*A61F 2/32* (2006.01)
(52) U.S. Cl. .................. 623/22.46; 623/22.42
(58) Field of Classification Search ............ 623/22.46, 623/22.15, 22.4, 22.43, 22.44, 22.41, 23.11, 623/23.15, 23.21, 23.22, 23.26, 23.27, 23.14, 623/22.42
See application file for complete search history.

(56) References Cited

U.S. PATENT DOCUMENTS

| | | | | |
|---|---|---|---|---|
| 3,874,003 A | * | 4/1975 | Moser et al. | ............ 623/23.11 |
| 4,950,300 A | * | 8/1990 | Langlais | ................. 623/22.44 |
| 4,997,444 A | | 3/1991 | Farling | |
| 5,135,529 A | * | 8/1992 | Paxson et al. | ................. 606/85 |
| 5,458,647 A | * | 10/1995 | Brochier et al. | ......... 623/21.17 |

FOREIGN PATENT DOCUMENTS

| | | | | |
|---|---|---|---|---|
| DE | 29 33 237 | | 3/1981 | |
| DE | 44 43 051 | | 10/1996 | |
| DE | 4443051 | * | 10/1996 | ............. 623/22.46 |
| EP | 0 099 167 | | 1/1984 | |
| EP | 0 170 779 | | 2/1986 | |
| EP | 0 420 435 | | 4/1991 | |
| EP | 0420435 | * | 4/1991 | ................ 623/22.4 |
| EP | 1 013 242 | | 6/2000 | |
| EP | 1013242 | * | 6/2000 | ................ 623/2.46 |
| EP | 1 080 701 | | 3/2001 | |
| FR | 2.105.998 | | 4/1972 | |
| FR | 2 580 170 | | 10/1986 | |
| FR | 2 653 660 | | 5/1991 | |
| GB | 2 045 082 | | 10/1980 | |
| GB | 2 319 962 | | 6/1998 | |
| WO | 91/18563 | | 12/1991 | |

(Continued)

*Primary Examiner*—Pedro Philogene
(74) *Attorney, Agent, or Firm*—Young & Thompson

(57) ABSTRACT

A conical coupling of a male member (10) and a female member (11), the male member (10) comprising a cone (12) ensleeved in a truncated conical portion (15) of a corresponding recess (14) formed in the female member (11), is characterized in that the female member (11) is made of a material having a Young's modulus at most equal to about 35 GPa and at most equal to that of the material from which the male member (10) is made, and in that a surface (13) of the male member perpendicular to the axis (A1) of the coupling is in contact with a surface (17) of the female member also perpendicular to the coupling axis such that the male and female members (10, 11) are in axial abutment against each other. The female member (11) is for example of pyrocarbon and the male member (10) of metal, ceramic or pyrocarbon.

21 Claims, 4 Drawing Sheets

FOREIGN PATENT DOCUMENTS

| | | | | |
|---|---|---|---|---|
| WO | WO9118563 | * 12/1991 | .............. | 623/22.42 |
| WO | 97/11651 | 4/1997 | | |
| WO | WO9712566 | * 10/1997 | .............. | 623/21.15 |
| WO | 02/13730 | 2/2002 | | |

* cited by examiner

CONICAL COUPLING AND PROSTHESIS COMPRISING SUCH A COUPLING

FIELD OF THE INVENTION

The present invention relates to a conical coupling of a male member and a female member, adapted to receive in particular axial compression loads. The coupling according to the invention finds particular application, but not exclusively, in the field of medical prostheses.

BACKGROUND OF THE INVENTION

Couplings of the conical type, such as Morse cones, are a well-known solution to assemble two pieces in a simple and disassembleable way. A conical coupling is constituted, as shown in FIG. 1, by a male member 1 and a female member 2, generally of metal. The male member 1 comprises a cone 3 fitted in a corresponding conical recess 4 of the female member 2. The male and female members 1, 2 are designed such that, when they are in coupled position, interstices e1, e2 remain between the distal end of the cone 3 and the bottom of the conical recess 4 and between the base, 5, of the female member 2 and the upper plane or shoulder, 6, of the male member 1, so as to obtain a wedging of the cone 3 in the recess 4 and to avoid making the coupling hyperstatic. These interstices e1, e2 must remain over all the range of use of the coupling. In other words, the male and female members 1, 2 are designed to resist forces of penetration of the male member 1 into the female member 2 no matter what the axial compression loads that may be applied to the coupling.

This type of coupling ensures an effective centering and blocking in rotation of the male member relative to the female member. However, it requires producing the female member of a material that is very resistant in tension. Indeed, because of the angle of the cone 3 and of the axial compression force necessary to produce the coupling, i.e. to assemble the male and female members, the lower portion of the female member in contact with the cone 3 is permanently subjected to tension forces T, which increase when, during use, the coupling is subjected to axial compression loads F.

Thus, while such couplings are suitable for male and female members that are made of metal and which thus have high resistance in tension, their principle seems to be difficultly transposable to applications in which the coupling would be subjected to large axial compression loads F, such as those received for example by certain prostheses, and the material of which the female member would be made would have poor resistance in tension. In such cases, indeed, the female member would break at the level of its lower portion, under the action of tension forces T, as soon as the maximum tensile strength limit of the material constituting the female member is exceeded.

OBJECT OF THE INVENTION

The present invention seeks to provide a conical coupling whose female member is made of a material different from those generally used in conventional conical couplings and which is capable of limiting the tensile forces to which the female member is subjected even when axial compression loads are applied to the coupling.

To this end, there is provided according to the invention a conical coupling of a male member and a female member, the male member comprising a cone fitted in a truncated conical portion of a corresponding recess formed in the female member, characterized in that the female member is made of a material having a Young's modulus at most equal to about 35 GPa and at most equal to that of the material from which the male member is made, and in that a surface of the male member perpendicular to the axis of the coupling is in contact with a surface of the female member also perpendicular to the axis of the coupling such that the male and female members are in axial abutment against each other.

SUMMARY OF THE INVENTION

Thus, in the coupling according to the invention, and in contrast to conventional conical couplings in which interstices are necessarily left between the male and female members, the male and female members are in axial abutment against each other. The intensity of the tensile forces borne by the female member thus remains constant and in particular does not increase when the coupling is subjected to axial compression loads of increasing magnitude. The female member can accordingly be made of a material having poor resistance in tension.

This solution, in which the connection between the male member and the female member is deliberately hyperstatic, is made possible by the intrinsic resilience of the female member, or in other words by the low Young's modulus, less than or equal to about 35 GPa, of the material from which the female member is made, and by the fact that the female member is at least as resilient as the male member. Thanks to these properties, indeed, the female member can, during its assembly with the male member, be moved axially toward the male member along the cone of this latter, by resilient deformation, even after a wedging effect of the cone in the corresponding recess has been obtained. By dimensioning the male and female members such that the female member enters into axial abutment against the male member before exceeding the maximum tensile strength limit of the material constituting the female member, there can thus be obtained a conical coupling in which the cone of the male member is wedged in the recess of the female member, and is thus centered and blocked in rotation in this recess, and the tensile forces to which the female member is subjected remain limited to a fixed value lower than the above-mentioned maximum limit.

In typical embodiments of the coupling according to the invention, the female member is of pyrocarbon and the male member is of metal, ceramic or pyrocarbon.

The present invention also provides a prosthesis, for example a prosthesis for the head of the radius, a prosthesis for the head of the cubitus or a hip prosthesis, comprising a coupling as defined above, the female member of the coupling constituting a head of the prosthesis and the male member constituting a neck of the prosthesis, the prosthesis comprising moreover a tail.

The invention seeks moreover to provide a set of male and female members permitting providing the coupling as defined above.

To this end, there is provided according to the invention a set of male and female members, the male member comprising a cone adapted to be fitted in a truncated conical portion of a corresponding recess formed in the female member, characterized in that the female member is made of a material having a Young's modulus at most equal to about 35 GPa and at most equal to that of the material from which the male member is made, in that the male member comprises an abutment surface perpendicular to the axis of the cone, and in that the male and female members are so dimensioned that, when the male member and the female member are coupled to each other by fitting of the cone in the truncated conical portion of the recess, and under the effect of an axial compression load applied to this coupling and giving rise to axial displacement of the female member relative to the male member by resilient deformation of the female member after a wedging effect of the cone in the recess resulting from said fitting has been obtained, the female member can come into abutment against the abutment surface of the male member before the maximum tensile strength limit of the material from which the female member is made is exceeded.

BRIEF DESCRIPTION OF THE DRAWINGS

Other characteristics and advantages of the present invention will become apparent from the following detailed description of several embodiments of the invention, given with reference to the accompanying drawings, in which.

DETAILED DESCRIPTION OF THE INVENTION

In all the following description, as in the accompanying claims, there is meant by "fitting" a blocked adjustment of a male member in a female member.

Figure 1:
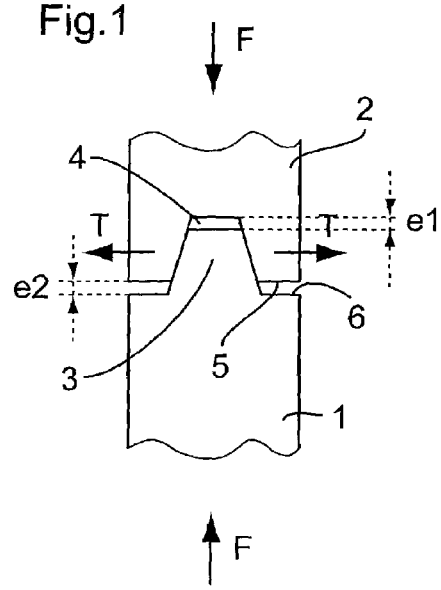
FIG. 1, already discussed, is a cross-sectional view of a conical coupling according to the prior art.
Figure 2:
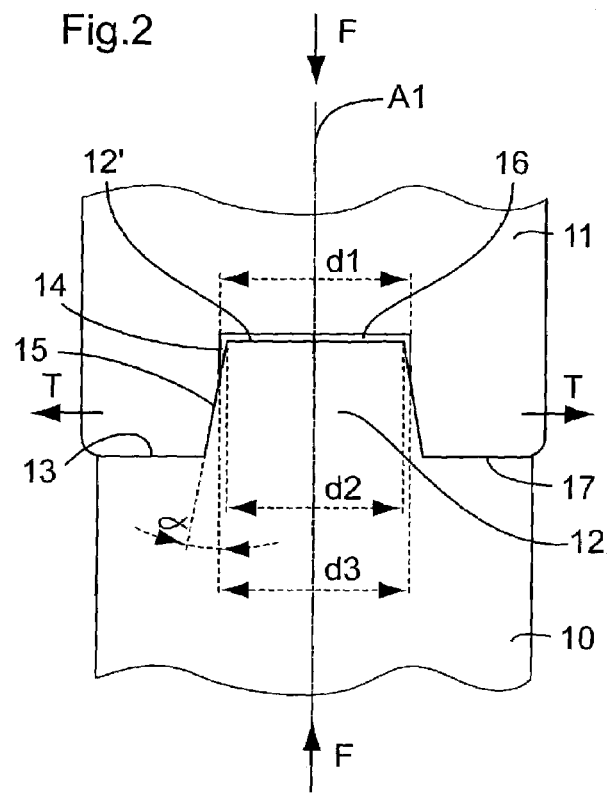
FIG. 2 is a cross-sectional view of a conical coupling according to a first embodiment of the invention.

FIG. 2 shows a conical coupling or fitting according to a first embodiment of the invention. This coupling comprises a male member 10 and a female member 11. The female member 11 is made of a material having a Young's modulus, or modulus of elasticity, less than or equal to about 35 GPa, for example comprised between about 10 GPa and about 35 GPa, and less than or equal to the Young's modulus of the material from which the male member 10 is made. By way of example, the female member 11 can be made of pyrocarbon and the male member 10 of metal, ceramic or pyrocarbon. Preferably, the material from which the female member 11 is made has a compressive strength, expressed in MPa, higher than its tensile strength.

The male member 10 comprises a cone 12 and a shoulder 13 serving as an abutment surface perpendicular to the axis A1 of the coupling, i.e. the axis of the cone 12. The cone 12 is wedged in a corresponding recess 14 in the female member 11 by fitting in a truncated conical portion 15 of this recess. Preferably, the recess 14 has, in addition to the truncated conical portion 15 in contact with the cone 12, a cylindrical clearance portion 16 prolonging the truncated conical portion 15 from the smaller diameter end of this latter, adjacent the bottom of the recess 14, and having a diameter d1 greater than or equal to the diameter d2 of the distal end 12' of the male cone 12. The cylindrical clearance portion 16 serves to receive the distal end 12' of the male cone 12, as shown in FIG. 2. So as to permit the insertion of this distal end 12' of the male cone 12 into the clearance portion 16, the small diameter d3 of the truncated conical portion 15 is also greater than or equal to the diameter d2.

The angle $\alpha$ of the male cone 12 is substantially identical to that of the truncated conical portion 15 of the recess 14. This angle is selected to be sufficiently large that the fitting of the male cone 12 within the recess 14 can be disassembled by the user by exerting a reasonable force, and sufficiently small that the male and female members 10, 11 remain firmly blocked relative to each other and that the female member 11 will not loosen from the male member 10 by rising along the cone 12 because of its elasticity. In practice, in the case particularly of a female member made of pyrocarbon, the cone angle $\alpha$ is typically comprised between 2.5 and 5°, and preferably equal to about 4°.

The base or proximal end surface 17 of the female member 11 is in contact with the shoulder 13 of the male member 10. Thus, the intensity of the tensile forces T to which the female member 11 is subjected, remains constant, and this even when the coupling is subjected to an axial compression load F of variable intensity.

Figure 3:
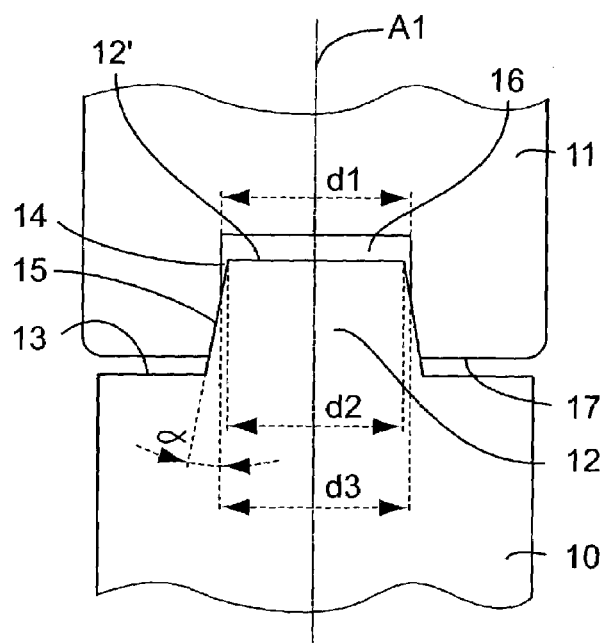
FIG. 3 is a cross-sectional view showing an intermediate condition of the coupling according to the first embodiment of the invention.

The coupling of FIG. 2 is obtained by assembling the male member 10 and the female member 11 such that the male cone 12 will be wedged in the recess 14 of the female member 11 to block the male and female members relative to each other, as shown in FIG. 3, then by applying a supplemental axial compression load to move the female member 11 axially relative to the male member 10 until its base 17 comes into bearing against the shoulder 13. During this axial displacement, the lower portion of the female member 11 in which the recess 14 is formed expands and thus is subject to tensile forces of increasing intensity, because of the cone angle $\alpha$, but these tensile forces no longer increase once the female member 11 has come into contact with the shoulder 13. The dimensions of the cone 12 and of the corresponding recess 14 are so selected that the base 17 of the female member 11 can come into abutment against the shoulder 13 before the maximum tensile strength limit of the material constituting the female member 11 is exceeded.

Figure 4:
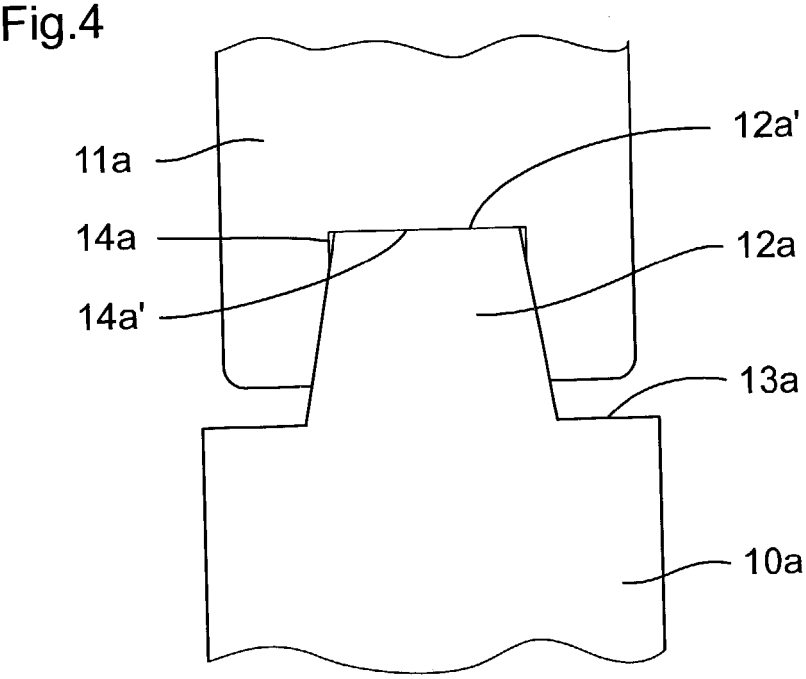
FIG. 4 is a cross-sectional view showing a conical coupling according to a second embodiment of the invention.

FIG. 4 shows a conical coupling according to a second embodiment of the invention. This coupling differs from that shown in FIG. 2 in that the abutment surface of the male member 10a is not constituted by the shoulder 13a but by the distal end surface 12a' of the cone 12a, which is in contact with the bottom 14a' of the recess 14a in the female member 11a. The coupling according to this second embodiment is better suited to female members whose base is narrow. It is obtained in a manner comparable to the coupling according to the first embodiment.

FIGS. 5 to 10 show prostheses using the coupling principles described above.

Figure 5:
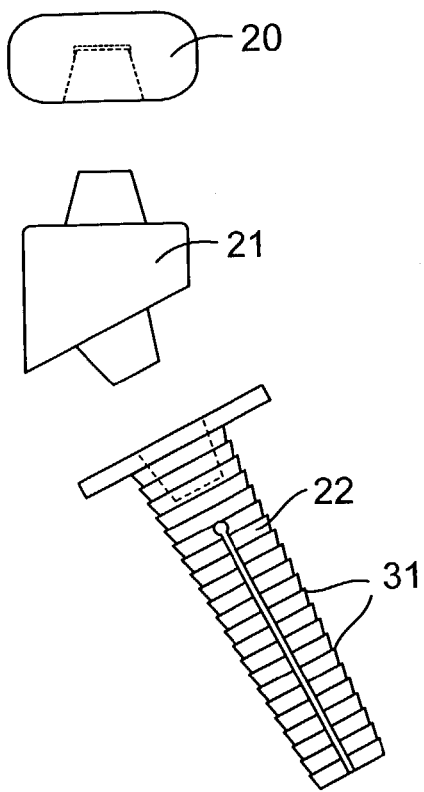
FIG. 5 is an exploded plan view showing a prosthesis of the head of the radius using the coupling according to the invention.

In FIG. 5 is shown a prosthesis for the head of the radius. This prosthesis is constituted by a pyrocarbon head 20, a metallic neck 21 and a metallic tail or extensible pin 22. The pyrocarbon constituting the head 20 is either solid or else in the form of a coating of pyrocarbon over a graphite substrate. The head 20 is adapted to replace the head of the radius and the tail 22 to be introduced into a hole provided in the radius.

Figure 6:
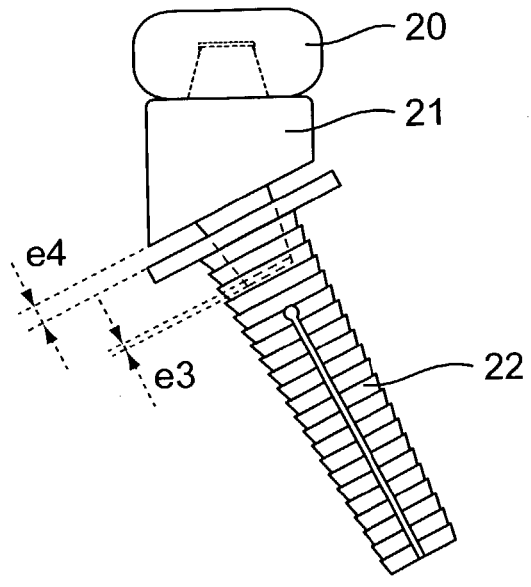
FIG. 6 is a plan view showing the prosthesis of FIG. 5 in an assembled condition.
Figure 7:
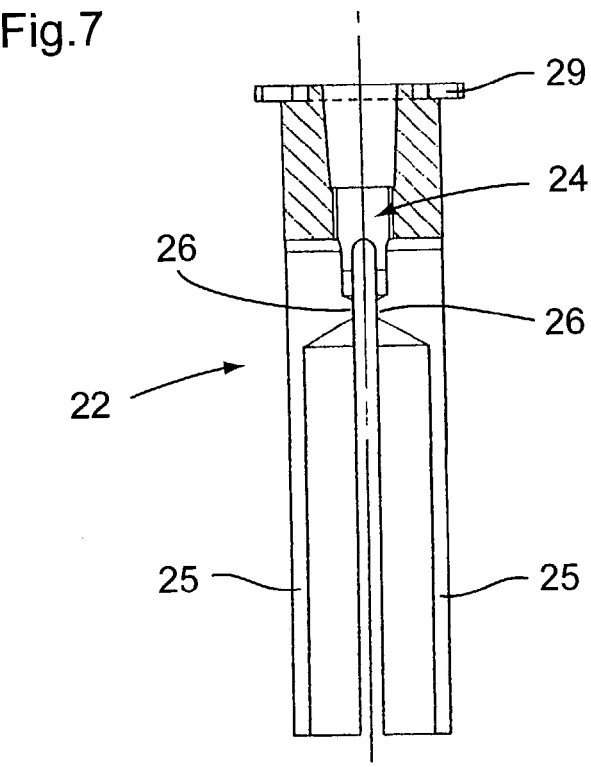
FIG. 7 is a cross-sectional view of an expansion pin constituting a tail of the prosthesis shown in FIG. 6.

The head 20 and the neck 21 form together a coupling of the type shown in FIG. 2, the head 20 playing the role of a female member having a recess at least a portion of which is truncated conical and the neck 21 of a male member having a cone and a shoulder or abutment surface against which the female member bears (cf. FIG. 6). This coupling could however, as a variant, be of the type shown in FIG. 4.

The tail 22 is coupled to the neck 21 by a conventional conical connection, leaving an interstice between the bottom of the recess of the female member, i.e. the tail 22, and the distal end of the cone of the male member, i.e. the neck 21, and between the base of the female member and the shoulder of the male member (cf. references e3, e4).

Thanks to this modular assembly, each element 20, 21, 22 of the prosthesis is interchangeable. Each element 20, 21, 22 can thus be designed in different sizes and can have, no matter what its size, a recess or male cones of identical shapes and sizes, such that a given element of the prosthesis can be interchanged with a same element of different size. It is thus possible for the surgeon, once the respective sizes of the head and the tail have been selected for a given patient, to choose the size of the neck so as to obtain an optimum positioning of the head relative to the humerus and the cubitus.

Figure 8:
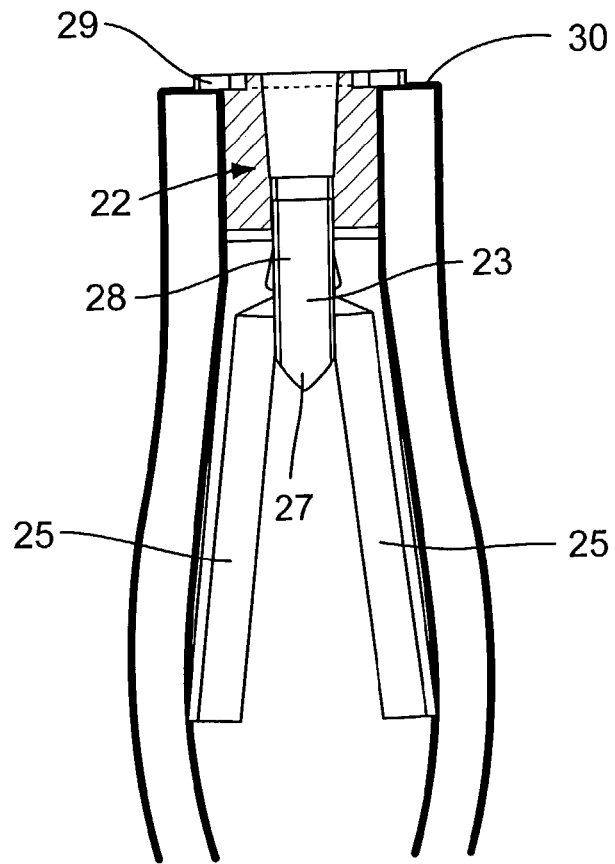
FIG. 8 is a cross-sectional view showing the expansion pin of FIG. 7, inserted in the radius.

According to another characteristic of the prosthesis for the head of the radius according to the invention, and so as to ensure effective anchoring of the prosthesis in the hole provided in the radius, the tail 22 is advantageously in the form of an expansible pin, adapted to deploy transversely when a screw 23 is inserted into it, as shown in FIG. 8. The tail 22 has more particularly an internal passage 24 having a threaded portion permitting the introduction and the screwing in of the screw 23, resiliently deformable legs 25 constituting the deployable portion of the tail, and internal projections 26 adapted to coact with a conical distal portion 27 of the screw 23 to space the legs 25 apart during introduction of the screw 23 and with a cylindrical portion 28 of the screw 23 to block the legs 25 in spaced position once the introduction of the screw 23 is completed (cf. FIGS. 7, 8). A flange 29 is moreover provided at the level of the proximal end of the tail 22, adapted to bear against a resected surface 30 of the radius. The external surface 31 of the tail 22 is preferably notched, as shown in FIGS. 5 and 6, so as to further increase the anchoring of this tail 22 in the hole of the radius.

Figure 9:
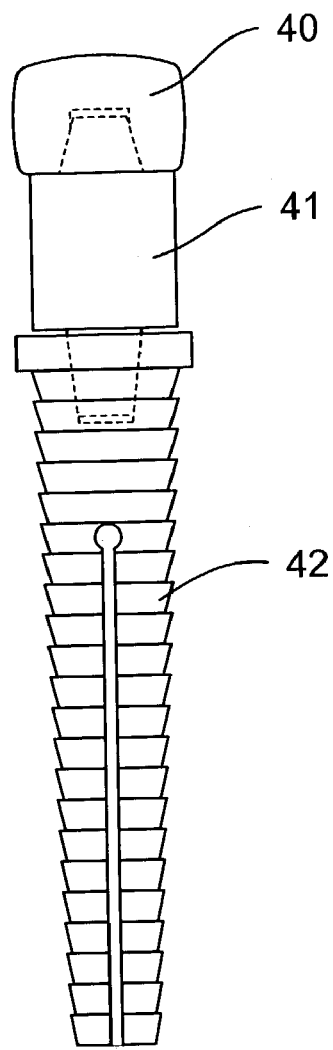
FIG. 9 is a plan view showing a prosthesis of the head of the cubitus using the coupling according to the invention.

FIG. 9 shows a prosthesis for the head of the cubitus. This prosthesis is constituted by a pyrocarbon head 40 adapted to replace the head of the cubitus, a metallic neck 41 and a metallic tail 42 adapted to be introduced into a hole provided in the cubitus. The head 40 and the neck 41 form a coupling of the type shown in FIG. 2. This coupling could however, as a variant, be of the type shown in FIG. 4. The neck 41 and the tail 42 are coupled to each other by a conventional conical coupling.

Figure 10:
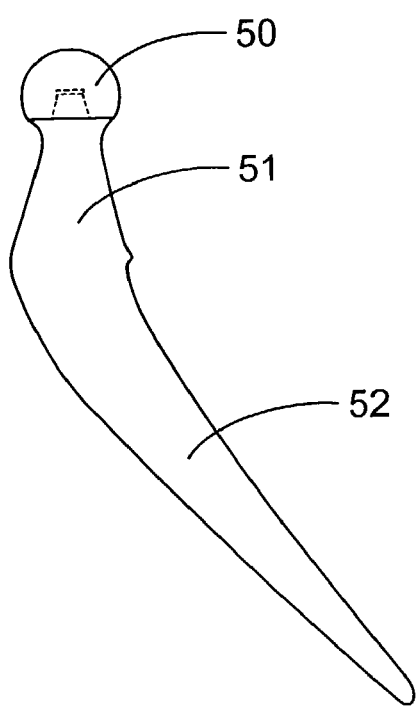
FIG. 10 is a plan view showing a hip prosthesis using the coupling according to the invention.

FIG. 10 shows a prosthesis of the hip, constituted by a pyrocarbon head 50, a metallic neck 51 and a metallic tail 52. The neck 51 and the tail 52 preferably form a single piece assembly. The head 50 and the neck 51 form a coupling comparable to that of FIG. 2, or, as a variant, to that of FIG. 4.

What is claimed is:

1. A conical coupling of a male member (10) and a female member (11), the male member (10) comprising a cone (12) fitted in a truncated conical portion (15) of a corresponding recess (14) formed in the female member (11), characterized in that the female member (11) is made of a material having a Young's modulus less than that of the material from which the male member (10) is made, and in that a surface (13) of the male member perpendicular to the axis (A1) of the coupling is in contact with a surface (17) of the female member also perpendicular to the axis of the coupling such that the male and female members (10, 11) are in axial abutment against each other.

2. A coupling according to claim 1, characterized in that said surface (13) of the male member perpendicular to the axis of the coupling is constituted by a shoulder of the male member (10) and said surface (17) of the female member perpendicular to the axis of the coupling is constituted by a base of the female member (11).

3. A coupling according to claim 1, characterized in that said surface of the male member (10a) perpendicular to the axis of the coupling is constituted by the distal end (12a') of the cone (12a) of the male member (10a) and said surface of the female member perpendicular to the axis of the coupling is constituted by the bottom (14a') of the recess (14a) of the female member (11a).

4. Coupling according to claim 1, characterized in that the female member (11) is of pyrocarbon.

5. A coupling according to claim 4, characterized in that the male member (10) is of metal, ceramic or pyrocarbon.

6. Coupling according to claim 1, characterized in that the material from which the female member (11) is made has a Young's modulus comprised between about 10 GPa and about 35 GPa.

7. Coupling according to claim 1, characterized in that the material from which the female member (11) is made is more resistant in compression than in tension.

8. Coupling according to claim 1, characterized in that the cone (12) of the male member (10) and the truncated conical portion (15) of the recess (14) of the female member (11) have substantially the same cone angle ($\alpha$), which is comprised between about 2.5° and about 50°.

9. Coupling according to claim 1, characterized in that the male member (10) and the female member (11) are pieces of a prosthesis.

10. Prosthesis comprising a coupling according to claim 1, the female member of the coupling constituting a head (20) of the prosthesis and the male member constituting a neck (21) of the prosthesis, the prosthesis comprising moreover a tail (22).

11. A prosthesis according to claim 10, characterized in that the tail (22) is coupled to the neck (21) by a conical coupling.

12. Prosthesis according to claim 10, characterized in that the tail (22) is in the form of an expansible pin.

13. A prosthesis according to claim 12, characterized in that the external surface (31) of the tail (22) is notched.

14. Prosthesis according to claim 10, characterized in that it consists of a prosthesis of the head of the radius (20–22), a prosthesis of the head of the cubitus (40–42), or a hip prosthesis (50–52).

15. A set of male and female members (10, 11), the male member (10) comprising a cone (12) adapted to be fitted in a truncated conical portion (15) of a corresponding recess (14) formed in the female member (11), characterized in that the female member (11) is made of a material having a Young's modulus less than that of the material from which the male member (10) is made, in that the male member comprises an abutment surface (13) perpendicular to the axis (A1) of the cone (12), and in that the male and female members are so dimensioned that, when the male member

(10) and the female member (11) are coupled to each other by fitting of the cone (12) in the truncated conical portion (15) of the recess (14), and under the effect of an axial compression load applied to this coupling and giving rise to axial displacement of the female member (11) relative to the male member (10) by resilient deformation of the female member after an effect of wedging of the cone (12) in the recess (14) resulting from said fitting has been obtained, the female member (11) can come into abutment against the abutment surface (13) of the male member (10) before the maximum tensile strength limit of the material from which the female member (11) is made is exceeded.

16. A set of male and female members according to claim 15, characterized in that the small diameter (d3) of the truncated conical portion (15) of the recess (14) of the female member (11) is at least equal to the diameter (d2) of the distal end (12') of the cone (12) of the male member (10) and in that the truncated conical portion (15) of the recess (14) of the female member (11) is prolonged at the level of its smaller diameter end (d3) by a clearance portion (16) of a diameter (d1) at least equal to the diameter (d2) of the distal end (12') of the cone (12) of the male member (10) and adapted to receive this distal end (12') when the female member (11) is in abutment against the abutment surface (13) of the male member (10).

17. Set of male and female members according to claim 15, characterized in that the female member (11) is of pyrocarbon and the male member (10) is of metal, ceramic or pyrocarbon.

18. Set of male and female members according to claim 15, characterized in that the material from which the female member (11) is made has a Young's modulus comprised between about 10 GPa and about 35 GPa.

19. Set of male and female members according to claim 15, characterized in that the material from which the female member (11) is made is stronger in compression than in tension.

20. Set of male and female members according to claim 15, characterized in that the cone (12) of the male member (10) and the truncated conical portion (15) of the recess (14) of the female member (11) has substantially the same cone angle ($\alpha$), which is comprised between about 2.5° and about 5°.

21. A set of male and female members according to claim 20, characterized in that the cone angle ($\alpha$) is about 4°.

* * * * *